United States Patent [19]

Privas

[11] Patent Number: 5,218,960
[45] Date of Patent: Jun. 15, 1993

[54] ELECTRO-STIMULATION APPARATUS
[75] Inventor: Yves Privas, Pompano Beach, Fla.
[73] Assignee: Laboratoires Deglaude, Bagneux, France
[21] Appl. No.: 731,227
[22] Filed: Jul. 17, 1991
[30] Foreign Application Priority Data Jul. 18, 1990 [FR] France ............... 90 09136

[51] Int. Cl.$^5$ .............................. A61N 1/08
[52] U.S. Cl. ............... 128/423 R; 128/419 PS; 128/419 PT; 128/422; 128/419 R
[58] Field of Search ............... 128/421, 422, 419 PS, 128/419 PT, 423 R, 419 R, 908

[56] References Cited
U.S. PATENT DOCUMENTS

| | | | |
|---|---|---|---|
| 4,024,875 | 5/1977 | Putzke | 128/423 R |
| 4,084,595 | 4/1978 | Miller | 128/422 |
| 4,096,866 | 6/1978 | Fischell | 128/419 PG |
| 4,112,923 | 9/1978 | Tomecek | 128/419 R |
| 4,157,087 | 6/1979 | Miller et al. | 128/422 |
| 4,174,706 | 11/1979 | Jankelson et al. | 128/422 |
| 4,197,850 | 4/1980 | Schulman et al. | 128/419 PS |
| 4,398,545 | 8/1983 | Wilson | 128/421 |
| 4,637,405 | 1/1987 | Brenman et al. | 128/421 |
| 4,926,864 | 5/1990 | Dufresne et al. | 128/421 |
| 4,981,146 | 1/1991 | Bertolucci | 128/421 |
| 5,069,211 | 12/1991 | Bartelt et al. | 128/421 |

FOREIGN PATENT DOCUMENTS 0145176 6/1985 European Pat. Off. .
0275213 7/1988 European Pat. Off. .

Primary Examiner—Kyle L. Howell
Assistant Examiner—Kennedy J. Schaetzle
Attorney, Agent, or Firm—Sughrue, Mion, Zinn, Macpeak & Seas

[57] ABSTRACT

Electro-stimulation apparatus comprises a self-contained housing including at least one energy source, a contact end for application against the skin of a user so as to transmit a series of repetitive electrical discharges to the skin, and means for stabilizing the current and the frequency of the discharges. When the energy source has worn to such an extent that the discharge current can no longer be stabilized, the apparatus stops working and must be discarded.

6 Claims, 3 Drawing Sheets

ELECTRO-STIMULATION APPARATUS

The present invention relates to electro-stimulation apparatus, and intended in particular to break smokers of the tobacco habit.

BACKGROUND OF THE INVENTION

Numerous methods have been tried in the field of breaking the tobacco habit. By way of example, mention may be made of medicines based on lobeline, quinine, and nicotine, and systems such as acupuncture or auricular stimulation obtained by implanting needles or a clip or by electrical stimulation.

Installing a clip suffers from the drawback of needing to be performed by a specialist. It may give rise to discomfort. It provides permanent stimulation and that is not necessary.

Implanting needles is a difficult method which must be performed by a specialist under Draconian hygiene conditions.

Electrical stimulation offers certain advantages since it is not essential for it to be performed by a specialist, the effect is powerful and fast acting, it is completely hygienic, and stimulation can be applied each time the need is felt.

Presently known electrical stimulation apparatuses as used in the state of the art are mainly fixed apparatuses powered by mains and suitable for use by specialists, only.

There are other, transportable apparatuses capable of being powered from a renewable source of energy. Some comprise a housing connected to a contact pencil via a cord, while other include a contact point.

When a user makes use thereof by application on some number of accurately-specified stimulation points, the pencil or contact point transmits a series of electrical impulses that are interpreted by the nervous system as feeling like "pins and needles" (formication).

However, these apparatuses are not always effective; their operation may be disturbed by a certain number of factors both with respect to connector reliability in the apparatus/cord link when such a link is provided, and more generally with respect to instability in various electrical magnitudes caused by changes in the level of charge in the renewable energy source.

SUMMARY OF THE INVENTION

The Applicant has recently discovered that stabilizing said electrical magnitudes, in particular frequency and peak current, on constant values regardless of the level of charge in the energy charge greatly improves the effectiveness of electrical stimulation devices of the kind in question. The specifications of the energy source constitute an integral feature of the overall system.

The present invention provides an electro-stimulation apparatus that implements the above discovery, and that preferably includes other advantageous characteristics as specified below.

The present invention thus provides an electro-stimulation apparatus comprising a self-contained housing including at least one energy source and a contact end for application against the skin of a user so as to transmit a series of repetitive electrical discharges to the skin, the apparatus further including means for stabilizing at least one parameter characterizing the series of discharges. Said means for stabilizing at least one parameter characterizing the series of discharges may stabilize the frequency of the discharges and/or the maximum electrical current of the discharges. The apparatus may include a first indicator means for indicating that the apparatus is working. The apparatus may also include second indicator means for indicating that the energy source has worn to such an extent that the discharge current can no longer be kept constant. Advantageously, the apparatus also includes means for stopping the emission of electrical discharges when it is detected that the source of energy is so low worn that discharge current can no longer be kept constant.

Advantageously, the housing is closed so as to prevent it being opened by a user, thereby ensuring that the user cannot replace the energy source after the emission of electrical discharges has been stopped due to the apparatus detecting that its energy source has worn to a point where the discharge current can no longer be kept constant.

The housing may contain an electronic circuit comprising a power supply connected to an oscillator and a low voltage detection circuit, itself connected to said second indicator means and to the oscillator so that when the low voltage detection circuit detects a power supply voltage below a certain threshold, said low voltage detection circuit applies a signal to the oscillator to prevent the oscillator operating, and causes a "voltage low" signal to be emitted by said second indicator means, said oscillator being connected to a control circuit for amplifying a periodic output signal from the oscillator, said control circuit itself being connected to said first indicator means to emit an "apparatus working" signal, and said control circuit also being connected to a voltage converter circuit for raising the voltage of the signal amplified by the control circuit, said converter circuit being provided with a circuit for regulating the current of the electrical discharges and being connected to an electrode that extends to the contact end.

Advantageously, the first indicator means and the second indicator means are constituted by a two-color light-emitting diode (LED) capable of emitting light of two different colors, the first color indicating that the power supply voltage is too low, and the second color indicating that the apparatus is working.

BRIEF DESCRIPTION OF THE DRAWINGS

An embodiment of the invention is described by way of example with reference to the accompanying drawings, in which.

DETAILED DESCRIPTION

Figure 1:
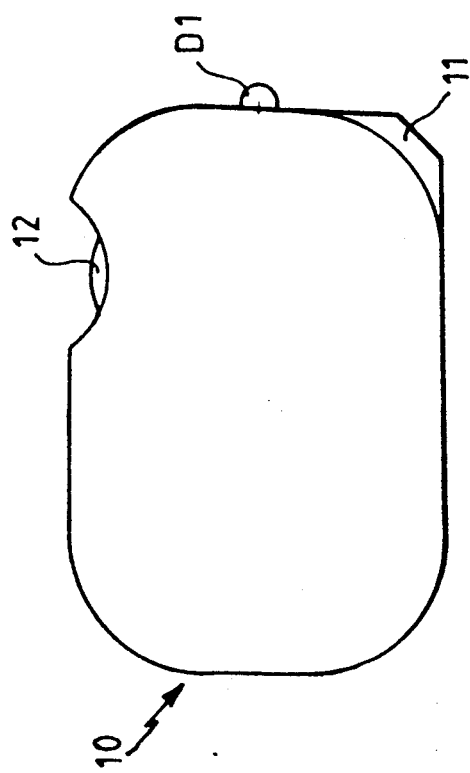
FIG. 1 is a side view of a housing of a preferred embodiment of the invention.
Figure 2:
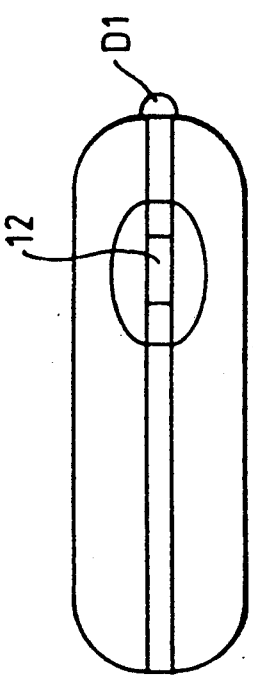
FIG. 2 is a plan view of the FIG. 1 housing.

FIGS. 1 and 2 show the outside shape of one example of an electro-stimulation apparatus of the invention. It is in the form of a flat housing 10 of a size suitable for holding in the hand, having two faces that are substantially rectangular with rounded corners. A contact end 11 extends from one of the rounded corners. The housing also includes a control knob 12 and an indicator, preferably a two-color LED D1 capable of emitting green light or red light.

On feeling the need to smoke, a user should apply the contact end 11 against a point of the skin, preferably on an ear, and rotate the control knob 12. Rotating the control knob 12 has the effect of triggering the emission of electrical pulses via the contact end 11, and of adjusting the peak current of said pulses. When the apparatus is working, this is displayed by a flashing green light emitted by the LED D1.

In this example, the housing is 8 cm long, 5.2 cm wide, and 2.4 cm thick. It is thus easily slid into a pocket in clothing and thus remains on hand for a user whenever the need to smoke is felt.

The electro-stimulation apparatus runs on batteries. When the batteries are so worn that the discharge current can no longer be kept constant by the apparatus, then the LED D1 displays a continuous red light and the emission of electrical pulses is stopped. The apparatus should then be thrown away.

The housing 10 cannot be opened without being damaged, thereby preventing the user changing the batteries. This prevents the user replacing the worn batteries by different batteries which could have electrical characteristics that are sufficiently different from those of the initial batteries to compromise the effectiveness of the apparatus.

To enable the apparatus to deliver electrical discharges at a current that is high enough, it is essential for the batteries to have low internal resistance. The batteries could be alkaline-manganese type batteries, but zinc-carbon batteries having the same nominal voltage would not be suitable.

Figure 3:
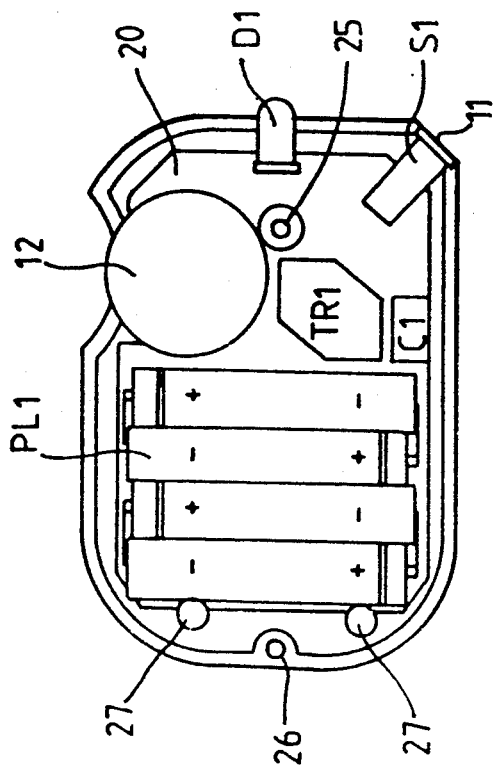
FIG. 3 is a side view of the FIG. 1 housing when open, showing a first face of a board for supporting the electronic circuit of the apparatus.
Figure 4:
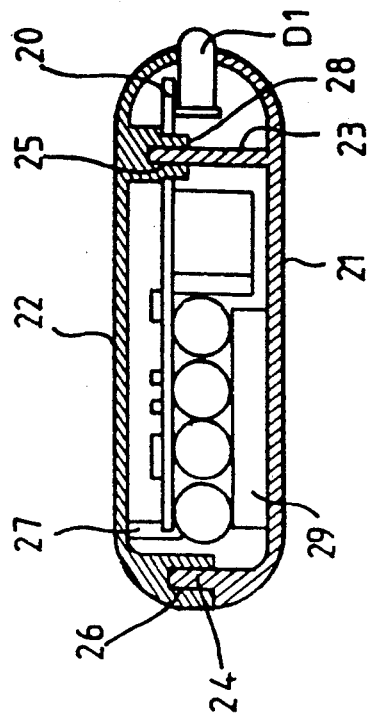
FIG. 4 is a section view of the FIG. 1 housing on line IV—IV.

FIGS. 3 and 4 show the internal disposition of the housing 10. The housing 10 comprises two shells 21 and 22 which are assembled together in such a manner as to prevent them being separated by a user. For example, the shell 21 may include two tenons 23 and 24 adapted to engage in corresponding mortises 25 and 26 formed in the shell 22. The tenons and mortises are permanently fixed together by means of glue.

A support board 20 is fixed inside the housing 10 and carries various electronic components. An electrical circuit is printed thereon. The support board may be fixed by any conventional means. For example, the shell 22 may have two resilient arms 27. Each arm 27 extends from the body 22 to an end having a notch adapted to receive an edge of the board 20 in snap-fastening engagement. In addition, the board 20 is pierced by a hole, and the shell 22 includes a stud 28 having a shoulder, said stud being adapted to engage in the hole through the board 20. The board 20 is thus installed by engaging the stud 28 through the hole in the board 20 until its shoulder comes into abutment therewith, and by simultaneous snap-fastening engagement with the resilient arms 27.

The board 20 has two faces, with a first one of the faces being shown in FIG. 3. Batteries PL1 are fixed on this first face, in this case four 1.5 V alkaline-manganese batteries that are connected in series, and this face also carries the knob 12, the LED D1, a transformer TR1 with a capacitor C1 whose function is described below, and an output electrode S1 extending to the contact end 11. The shells 21 and 22 include openings to allow the knob 12, the LED D1, and the electrode S1 to pass through the housing. The shell 23 also includes a rib 29 for holding the batteries PL1 in place.

Figure 5:
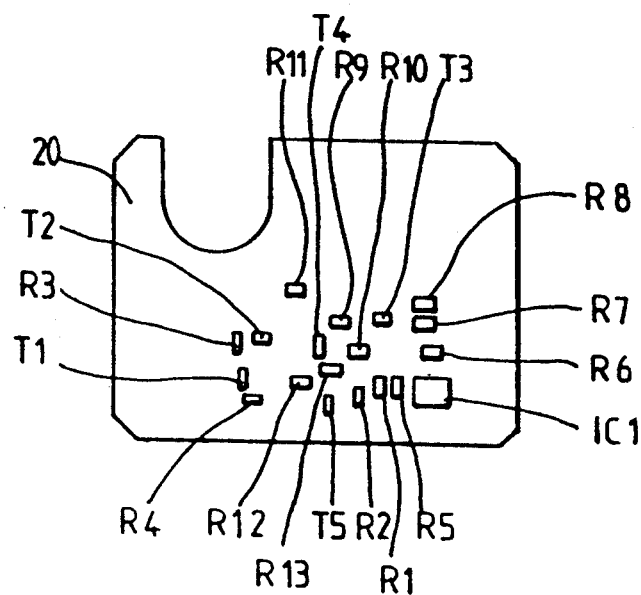
FIG. 5 is a view of the second face of the FIG. 3 support board, on a slightly smaller scale.

A second face of the support board 20 is shown in FIG. 5. An electrical circuit (not shown) is printed on this face and the various electronic components described in detail below are connected thereto.

Figure 6:
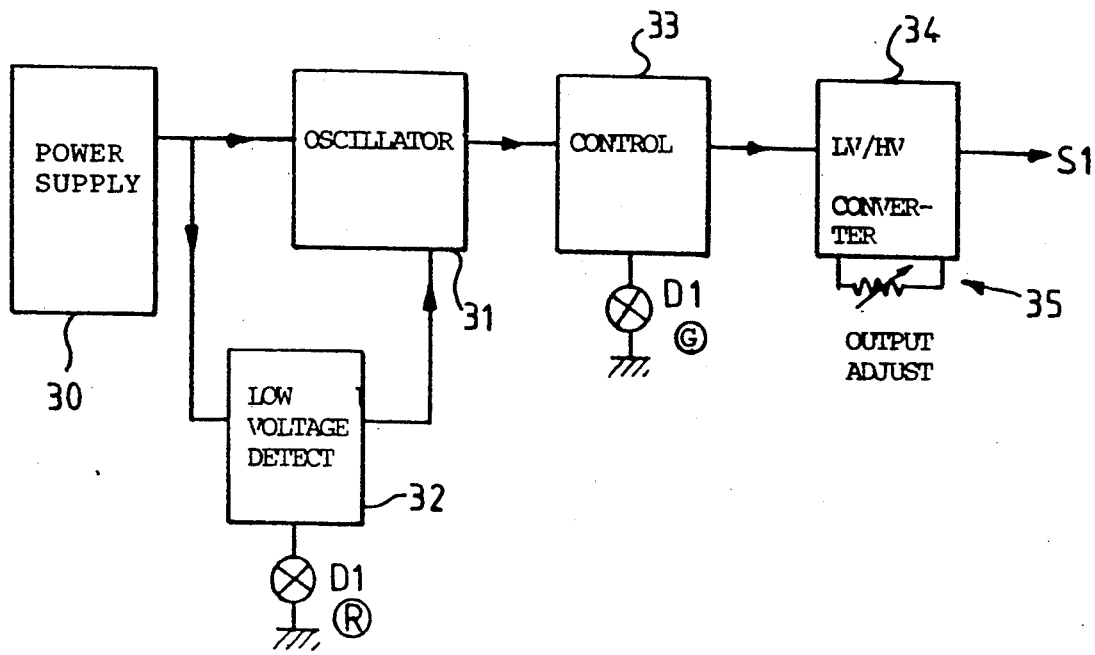
FIG. 6 is a block diagram of the electronic circuit in the embodiment of the invention shown in FIGS. 1 to 5.

FIG. 6 is a block diagram of the electronic circuit for the embodiment of the invention shown in FIGS. 1 to 5. This circuit includes an electrical power supply 30 connected to an oscillator 31 and to a low voltage detection circuit 32 which is in turn connected to the oscillator 31 and to the LED D1. When the circuit 32 detects that the voltage at the output from the power supply 30 is below a certain threshold, it causes the two-color LED D1 to shine with a red light and it applies a "voltage low" signal to the oscillator 31.

The oscillator 31 is connected to a control circuit 33. So long as the oscillator does not receive said "voltage low" signal, it transmits electrical pulses to the control circuit 33 at a frequency lying in the range 3 Hz to 8 Hz, for example. On receiving said "voltage low" signal, the oscillator 31 ceases to transmit electrical pulses to the control circuit 33. The control circuit 33 is connected to the light-emitting diode D1 and to the low voltage to high voltage converter circuit 34. On receiving pulses, the control circuit 33 transmits a series of pulses having greater electrical power to the circuit 34, and it also causes the two-color LED D1 to emit flashes of green light. The converter circuit 34 raises the voltage of the electrical pulses, e.g. up to 500 V, and it transmits them to the output electrode S1 31. In addition, the circuit 34 is connected to a circuit 35 for adjusting the electrical current in the pulses emitted by the electrode S1.

Figure 7:
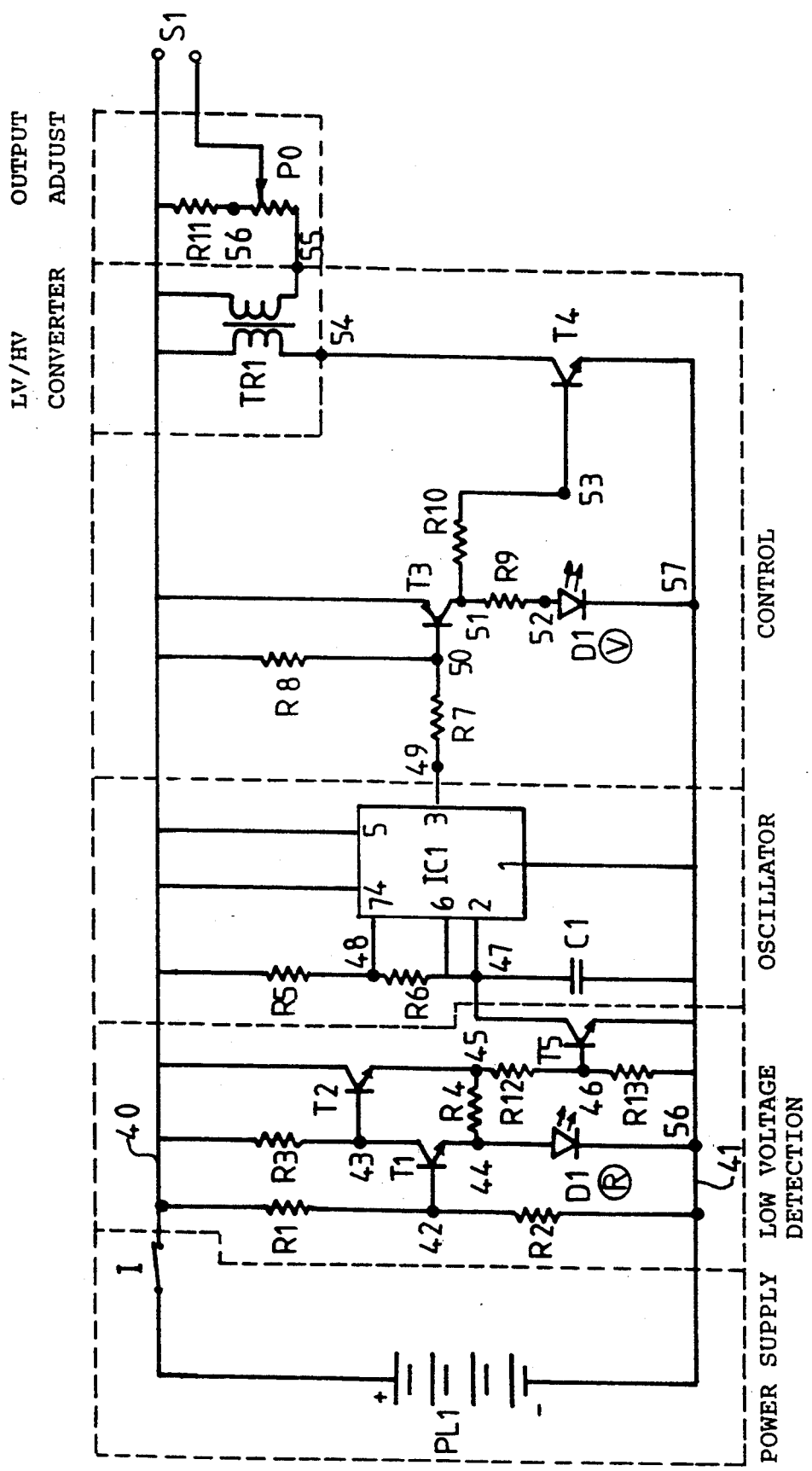
FIG. 7 is a detailed circuit diagram of the FIG. 6 electronic circuit.

FIG. 7 is a detailed circuit diagram of the FIG. 6 electronic circuit. The power supply circuit is constituted by four alkaline-manganese type 1.5 V batteries PL1 connected in series so as to produce a nominal voltage of 6 V. A switch I is connected in series with the batteries PL1. Advantageously, the switch is constituted by an end-of-stroke contact of the knob 12.

Two power supply rails 40 and 41 leave the power supply circuit. The following are connected between the two power supply rails 40 and 41.

Firstly the low voltage detection circuit which comprises:

two resistors R1 and R2 connected as a voltage divider, the resistor R1 being connected to rail 40, and the resistor R2 being connected to the resistor R1 at a point 42 and to the rail 41. In this example, R1 has a resistance of 33 kΩ and R2 has a resistance of 43 kΩ;

an NPN type transistor T1 having its base connected to the point 42;

a resistor R3 of resistance 15 kΩ connected to the collector of transistor T1 at a point 43, and to rail 40;

an NPN type transistor T2 whose base is connected to the point 43 and whose collector is connected to the line 40;

a resistor R4 of resistance 33 kΩ connected between a point 44 at the emitter of transistor T1 and a point 45 at the emitter of transistor T2;

the two-color LED D1 whose red-light terminal is connected to point 44 and which has another terminal connected to rail 41 at a point 56;

two resistors R12 and R13 connected as a voltage divider. In this example, the resistance of R12 is 10 kΩ and the resistance of R13 is 3.8 kΩ. Resistor R12 is connected to point 45 and resistor R13 is connected to resistor R12 at a point 46 and to rail 41; and NPN transistor T5 whose base is connected to the point 46, whose emitter is connected to rail 41, and whose collector is connected to a point 47 of the oscillator circuit.

The oscillator circuit which comprises:

an astable multivibrator IC1 having seven connection terminals, two of which terminals 4 and 5 are both connected to rail 40, one terminal 1 is connected to rail 41, and an output terminal 3 is connected to a point 49 of the control circuit;

a resistor R5 connected between the rail 40 and a point 48 connected to terminal 7 of multivibrator IC1, the resistance of R5 being 160 k$\Omega$;

a resistor R6 connected to terminals 2 and 6 of multivibrator IC1, with the resistance of R6 being 47 k$\Omega$; and a capacitor C1 of capacitance 1 $\mu$F connected between the point and rail 41.

The control circuit which comprises:

a resistor R7 having a resistance of 10 k$\Omega$ and connected to point 49;

a resistor R8 having a resistance of 10 k$\Omega$ connected to the resistor R7 at a point 50 and to rail 40;

a PNP type transistor T3 having its base connected to point 50 and its emitter connected to rail 40;

a resistor R9 of resistance 100 $\Omega$ connected at a point 51 to the collector of transistor T3;

the two-color LED D1 whose green-light terminal is connected to the resistor R9 at a point 52 and whose other terminal is connected to rail 41 at a point 57;

a resistor R10 of resistance 410 $\Omega$, connected to point 51; and an NPN type transistor T4 whose base is connected to resistor R10 at a point 53, whose emitter is connected to rail 41, and whose collector is connected to the voltage converter circuit at a point 54.

The voltage converter circuit comprises a transformer TR1 having a primary winding and a secondary winding. The primary winding is connected between rail 40 and point 54, while the secondary winding is connected between rail 40 and a point 55 in common with the output-adjustment circuit. The voltage between the point 55 and the rail 40 is 500 V in this case.

The output-adjustment circuit for adjusting the peak current of electrical pulses emitted by the electrode S1 comprises:

a resistor R11 of resistance 220 k$\Omega$ connected between rail 40 and a point 56; and a potentiometer Po controlled by the knob 12 and connected between the point 55 and the point 56, said potentiometer including an output connected to one terminal of electrode S1, with another terminal of electrode S1 being connected to the rail 40.

When the switch I is closed and the batteries PL1 deliver a voltage greater than a limit voltage, e.g. 4.2 V, a low current flows through resistors R4, R12, and R13, so that the voltage between point 44 and rail 41 is too small to cause LED D1 to emit red light. In addition, because of the low current flowing through R13, the potential at point 46 is not sufficient to cause transistor T5 to be saturated. Capacitor C1 is therefore not short circuited.

The multivibrator IC1 associated with resistors R5 and R6 and with capacitor C1 delivers a low power signal at its output 3 in the form of a periodic square-wave voltage signal having a frequency equal to 5 Hz, for example. If Vo is the voltage produced by the batteries PL1, the potential difference between rail 41 and output 3 varies periodically between +Vo and −Vo at the frequency of 5 Hz in this particular example.

When the potential difference between rail 41 and output 3 is +Vo, the output 3 is at the same potential as rail 40. No current therefore flows through resistors R8 and R7. The point 50 connected to the base of transistor T3 is therefore at the same potential as rail 40 which is connected to the emitter of transistor T3. No current can therefore flow between the emitter and the collector of transistor T3. No current therefore flows between the points 52 and 57. The LED does not emit green light. Since the point 53 is then at the same potential as rail 41, transistor T4 is off, such that the primary winding of transistor TR1 has no current flowing through it. No voltage is therefore delivered at the terminals of the secondary winding of transistor TR1, and thus no current is output to electrode S1 in contact with the skin of the user.

When the potential difference between output 3 from the multivibrator and rail 41 is −Vo, current flows through the resistors R8 and R7 towards said output 3. The point 50 connected to the base of transistor T3 is therefore at a potential that is lower than rail 40 which is connected to the emitter of transistor T3. Transistor T3 is therefore switched on, such that current flows through it from the emitter to the collector. Current therefore flows through the resistor R9 and the LED D1 between points 52 and 53 so the LED emits green light. The point 51 and thus the point 53 connected to the base of transistor T4 are therefore at a higher potential than rail 41 which is connected to the emitter of transistor T4 which therefore switches on. Current thus flows through transistor T4 between its collector and its emitter, also flowing through the primary winding of transformer TR1. The magnitude of this current is set by the current flowing through the transistor T4 from its base to its emitter, which current depends on resistor R10.

Transformer TR1 raises voltage so that it delivers voltage pulses at 500 V between rail 40 and the point 55, the pulses having a frequency of 5 Hz in this particular example.

These voltage pulses are transformed into pulses of current flowing through the circuits constituted by the resistor R11, the potentiometer Po, and the skin of the user between the terminals of electrode S1.

The maximum value of the output current flowing through the skin of the user between the terminals of electrode S1 is fixed by the potentiometer Po under the control of the knob 12.

When the voltage at the terminals of batteries PL1 falls below 4.2 V, transistor T1 becomes saturated. The potential at point 44 therefore increases sufficiently to cause LED D1 to emit red light, and because of the larger current flowing through resistor R13, the potential at point 46 increases sufficiently to saturate transistor T5, thereby short circuiting capacitor C1 and thus stopping the oscillator whose output 3 remains at the voltage +Vo. The apparatus can therefore no longer deliver electrical output pulses via electrode S1, and should therefore be discarded.

The value 4.2 V corresponds to each battery providing a voltage of 1.05 V. This limit voltage therefore does not correspond to the batteries being completely worn out in which case the voltage across the terminals of each battery would be closer to 0.8 V, but corresponds to the batteries being worn to such an extent that the current in the electrical discharges can no longer be kept constant. At this level of wear, only one-half of the energy that could normally be delivered from the batteries has been consumed, however the internal resistance of the batteries which increases with decreasing voltage across the battery terminals is now too high to enable enough electrical current to be delivered to ensure that the stimulation is effective.

I claim:

1. A pocket size, non-invasive electro-stimulation apparatus for breaking the tobacco habit, comprising: a self-contained housing containing at least one battery connected to electrical discharge means for emitting a series of repetitive electrical discharges, and a contact end (11) connected to said electrical discharge means for external application against the skin of a user so as to transmit said series of repetitive electrical discharges to the skin, wherein the apparatus includes a low voltage detection circuit means (32) for detecting a drop in the voltage from the battery to below a predetermined value whereat the apparatus is no longer able to output a constant discharge current, said low voltage detection circuit means having means for stopping said electrical discharge means in the event of said drop in the voltage of the battery below said predetermined value being detected so as to prevent the apparatus from operating as soon as the electrical discharge current can no longer be kept constant.

2. Electro-stimulation apparatus according to claim 1, wherein the housing comprises two shells with means for permanently fixing together said shells, so as to prevent the housing being opened by a user, thereby preventing the user replacing the battery after electrical discharging has been stopped following the detection of the voltage from the battery dropping below said predetermined value.

3. An electro-stimulation apparatus according to claim 1, further including indicator means for indicating that the apparatus is working.

4. Electro-stimulation apparatus according to claim 1, further including "voltage low" indicator means for indicating that the voltage from the battery has dropped below said predetermined value.

5. Electro-stimulation apparatus according to claim 1, wherein the electrical discharge means comprises an oscillator, and wherein the housing contains an electronic circuit comprising a power supply (30) connected to said oscillator (31) and to said low voltage detection circuit means, itself connected to "voltage low" indicator means (D1) and to said oscillator in such a manner that when the low voltage detection circuit means detects a power supply voltage lower than a certain threshold, said low voltage detection circuit means applies a signal to the oscillator to stop said oscillator operating and also causes a "voltage low" signal to be emitted by said "voltage low" indicator means, said oscillator being connected to control circuit means (33) for amplifying a periodic output signal from the oscillator, said control circuit means itself being connected to indicator means for indicating that the apparatus is working, and said control circuit means also being connected to a voltage converter circuit (34) for raising the voltage of the signal amplified by the control circuit means, said converter circuit being provided with an adjustment circuit (35) for adjusting the electrical discharge current and connected to an electrode (S1) extending to the contact end.

6. An electro-stimulation apparatus according to claim 5, wherein the means for indicating that the apparatus is working and the means for indicating the voltage is low are both constituted by a single two-color light-emitting diode capable of emitting two different colors: a first color indicating too low a power supply voltage, and a second color indicating that the apparatus is working.

* * * * *